United States Patent [19]
Wengyn et al.

[11] Patent Number: 5,303,822
[45] Date of Patent: Apr. 19, 1994

[54] RECEPTACLE TO SUPPORT AND RETAIN A PLURALITY OF USED HYPODERMIC NEEDLE AND SYRINGE COMBINATIONS

[76] Inventors: Mark D. Wengyn, 1543 Highcrest Cir.; Charles F. Brown, 2201 Cherokee Trail, both of Valrico, Fla. 33594

[21] Appl. No.: 8,625
[22] Filed: Jan. 25, 1993

Related U.S. Application Data

[63] Continuation-in-part of Ser. No. 819,057, Jan. 10, 1992, Pat. No. 5,184,721.

[51] Int. Cl.⁵ ............................................... A61L 2/16
[52] U.S. Cl. ..................... 206/366; 206/443; 206/571; 211/60.1; 248/311.2
[58] Field of Search ..................... 206/204, 363–366, 206/443, 446, 571; 248/219.3, 311.2; 211/60.1

[56] References Cited

U.S. PATENT DOCUMENTS

| | | | |
|---|---|---|---|
| 920,225 | 5/1909 | Van Denburgh | 206/364 X |
| 2,012,380 | 8/1935 | Durham | 206/365 X |
| 2,093,537 | 9/1937 | Balint | 206/365 X |
| 2,925,100 | 2/1960 | Senger | 206/363 X |
| 2,935,285 | 5/1960 | Drom | 248/219.3 |
| 3,292,776 | 12/1966 | Penn | 206/366 X |
| 4,826,003 | 5/1989 | Levy | 206/443 X |
| 4,855,110 | 8/1989 | Markur et al. | 211/79 X |
| 4,936,449 | 6/1990 | Conard et al. | 206/366 |
| 5,020,665 | 6/1991 | Bruno | 206/366 |
| 5,024,865 | 6/1991 | Insley | 206/204 X |
| 5,184,721 | 2/1993 | Wergyn et al. | 206/366 |

*Primary Examiner*—Bryon P. Gehman
*Attorney, Agent, or Firm*—Arthur W. Fisher, III

[57] ABSTRACT

A receptacle to support and retain a plurality of used hypodermic needle and syringe combinations to prevent the accidental pricking of the care giver or patient after use comprising an outer receptacle support including a substantially cylindrical body having a centrally disposed substantially cylindrical canister recess and a plurality of peripherally disposed substantially cylindrical liquid retaining tube recesses formed therein to selectively receive and support an inner disinfectant canister and a plurality of substantially cylindrical liquid retaining tubes respectively wherein the inner disinfectant retaining canister includes a substantially cylindrical tube to operatively house a disinfectant solution therein and a penetrable membrane to receive the used hypodermic needles therethrough to support and retain the used hypodermic needles in the disinfectant solution for subsequent disposal of the used hypodermic needle and syringe combinations.

32 Claims, 7 Drawing Sheets

RECEPTACLE TO SUPPORT AND RETAIN A PLURALITY OF USED HYPODERMIC NEEDLE AND SYRINGE COMBINATIONS

CROSS-REFERENCE

This is a continuation-in-part application of application Ser. No. 819,057 filed Jan. 10, 1992, now U.S. Pat. No. 5,184,721.

BACKGROUND OF THE INVENTION

1. Field of the Invention

A receptacle to support and retain a plurality of used hypodermic needle and syringe combinations to prevent the accidental pricking of the care giver or patient for safe storage and disposal.

2. Description of the Prior Art

Numerous means for the disposal of contaminated medical instruments have been developed. Such devices often provide containers to receive contaminated medical instruments deposited for disposal. It is important that such disposal devices reduce the extent reasonably obtainable the likelihood that the contaminated medical instruments will subsequently accidentally puncture someone and that contaminants will escape from the disposal container.

U.S. Pat. No. 4,936,449 discloses a block of styrofoam for penetration by and for frictionally holding, disposable hypodermic needles, scalpels and other sharps, held in a container including a bottom and a sidewall. Pawl-shaped projections are provided adjacent the upper lip of the sidewall. A lid includes complementary pawl-shaped projections adjacent its lower lip for engagement with respective projections on a contaminant neutralizing substance such as BETADINE, or another layer of, for example, wadding, located above or below the styrofoam can be saturated with the contaminant neutralizing substance. The sharps are protected only when the lid is plaCED ON THE CONTAINER. When so assembled, additional sharps cannot be introduced into the block.

U.S. Pat. No. 2,093,537 describes a medical case having a housing and removable cap. The body has a center hole open at the top and two narrower holes at the sides thereof configured to receive respective medical instruments. Sealing plugs are provided to seal the hole.

U.S. Pat. No. 478,081 shows a three cylindrical vessel to retain liquid and syringe. The case then serves as a sealed vessel to carry the medicated solution as well as the syringe. Annular stops are provided which engage the coupling of the needles and prevent their points from coming in contact with the bottoms of inclosing cylinders.

U.S. Pat. No. 5,024,865 teaches a closed sorbent shock or impact resistant container for shipping and storing hazardous liquid materials or a cryogenic container.

U.S. Pat. No. 4,919,264 describes a medical needle removing and disposing system comprising a box having a plurality of compartments therein, each for removing a needle assembly from injection and/or blood drawing equipment and for disposing of the needle assembly. A compartment comprises first and second containers for defining first and second chambers with a needle gripper positioned therebetween. The first container has a plastic, non-hardening, tacky, substance therein. Injection and/or blood drawing equipment with a medical needle assembly mounted thereon can be manipulated to extend a shaft of the needle assembly into the second chamber until a mounting tube of the medical needle assembly is located at the needle assembly remover which grips the mounting tube so that the injection and/or blood drawing equipment can be rotated for unscrewing the mounting tube from the injection and/or blood drawing equipment. The medical needle assembly is left in the dispenser with the shaft buried in the tacky substance.

U.S. Pat. No. 3,876,067 describes a collection box having a cover plate provided with a multiplicity of square openings into which a needle is inserted detachably fastened at a one-way-syringe whereby the head of the needle is caught behind the sharp-edged inside border of the opening and the syringe can be pulled off from the needle which is being held in position by a disinfectant filling into which the needle has been pierced.

U.S. Pat. No. 2,935,285 teaches an injection syringe container comprising a housing having a bottom wall, side walls, first and second end walls and a top wall. The top wall is formed with a longitudinal row of spaced openings, a pair of facing channel tracks secured upon and extending along the top wall and located at opposite sides of the longitudinal row of openings with upstanding tubes within the housing and fixedly mounted on the bottom wall.

Additional examples of the prior art are found in U.S. Pat. Nos. 2,738,872; 3,292,776; 4,015,810; 4,037,814; 4,327,060; 4,380,292; 5,020,665; Des. 229,048 and Des. 259,141.

SUMMARY OF THE INVENTION

The present invention relates to a receptacle to support and retain a plurality of used hypodermic needle and syringe combinations to prevent the accidental pricking giver or patient after use comprising an outer receptacle support configured to support an inner disinfectant canister and plurality of liquid retaining tubes in combination with a mounting means to mount the receptacle on a wall or other supporting surface.

The outer receptacle support comprises a substantially cylindrical body including a centrally disposed substantially cylindrical canister recess to selectively receive and support the inner disinfectant canister and a plurality of peripherally disposed substantially cylindrical liquid retaining tube recesses to selectively receive and support the plurality of liquid retaining tubes.

The inner disinfectant canister comprises a substantially cylindrical tube to operatively house a disinfectant solution therein and penetrable membrane to receive the used hypodermic needles therethrough to support and retain the used hypodermic needle and syringe combinations in the disinfectant solution. A substantially cylindrical protective sheath or sleeve is slidingly mounted in surrounding relationship relative to the substantially cylindrical tube. The substantive cylindrical protective sheath or sleeve is movable between a first or lower position to permit or allow placement of the used hypodermic needle and syringe combinations as described hereinafter and a second or upper position to encase or enclose the used hypodermic needle and syringe combinations therein after the care taker has completed the medical procedure.

The mounting means comprises a substantially cylindrical mounting sleeve to selectively secure the outer receptacle support and inner disinfectant canister to a wall or other support surface.

With the mounting means affixed to a wall or other supporting surface, the outer receptacle support and inner disinfectant canister are operatively mounted thereon.

In use, the care taker withdraws blood or other body fluids that are injected into one or more of the plurality of liquid retaining tubes operatively supported in the outer receptacle support. After the care taker has completed using the hypodermic needle and syringe combination and with the substantially cylindrical protective sheath or sleeve in the first or lower position, the hypodermic needle is forced through the penetrable membrane into the substantially cylindrical tube and submerged in the disinfectant solution to prevent accidental or inadvertant contact with the care taker or patient. The inner disinfectant canister may be removed from the outer receptacle support for disposal of the used hypodermic needle and syringe combinations with the substantially cylindrical protective sheath in the second or upper position.

Subsequently the plurality of liquid retaining tubes may be removed from the outer receptacle support for testing of the liquids stored therein.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
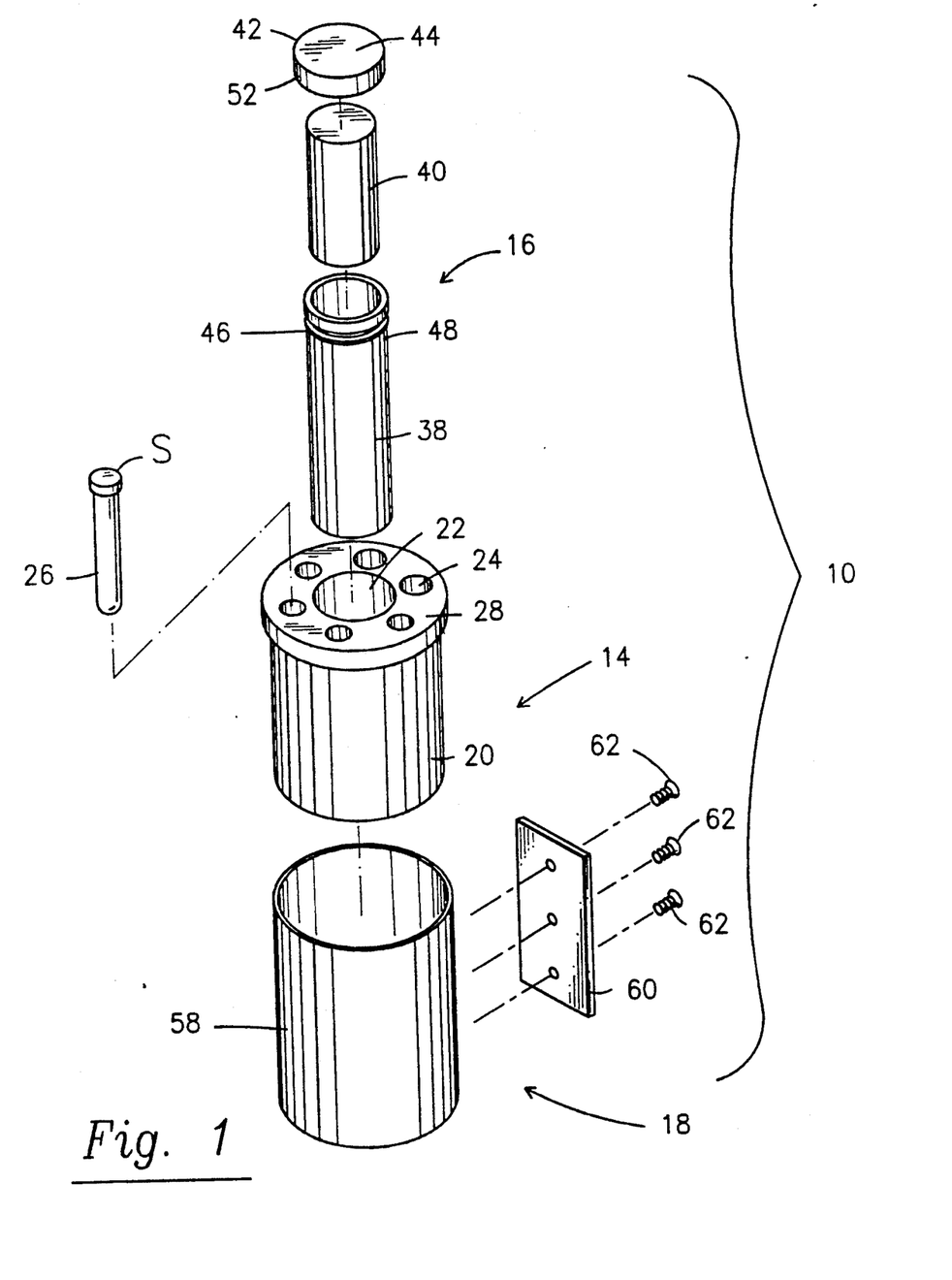
FIG. 1 is an exploded view of the receptacle of the present invention.
Figure 2:
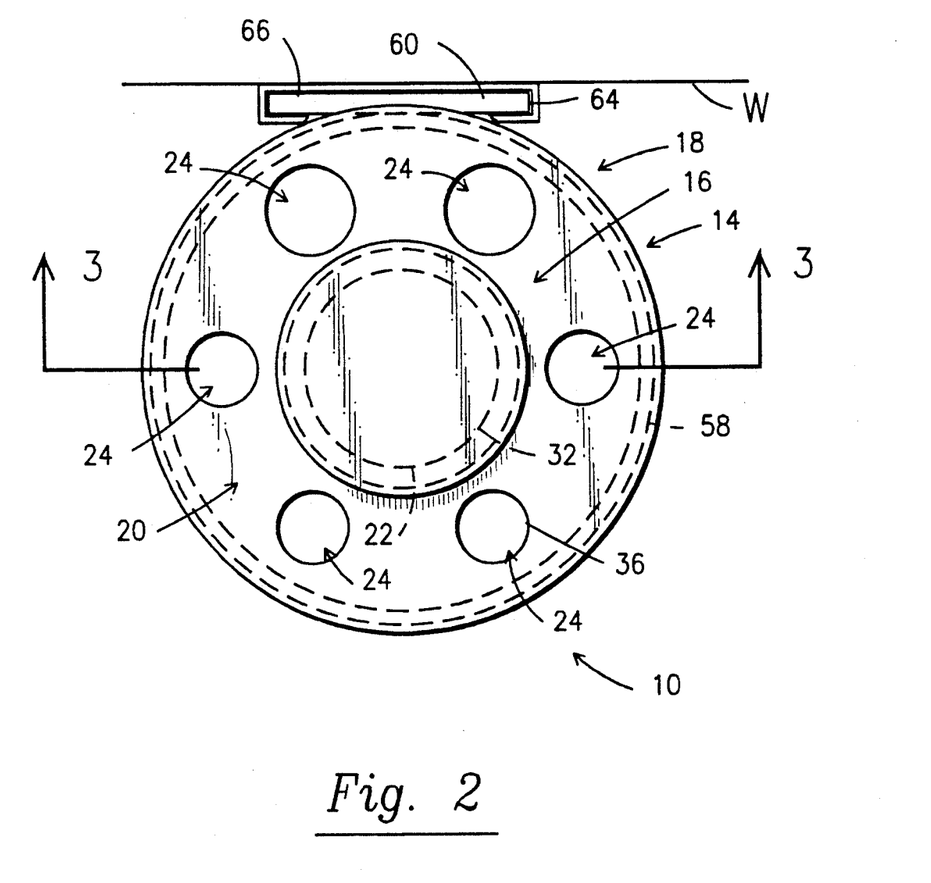
FIG. 2 is a top view of the receptacle of the present invention.
Figure 3:
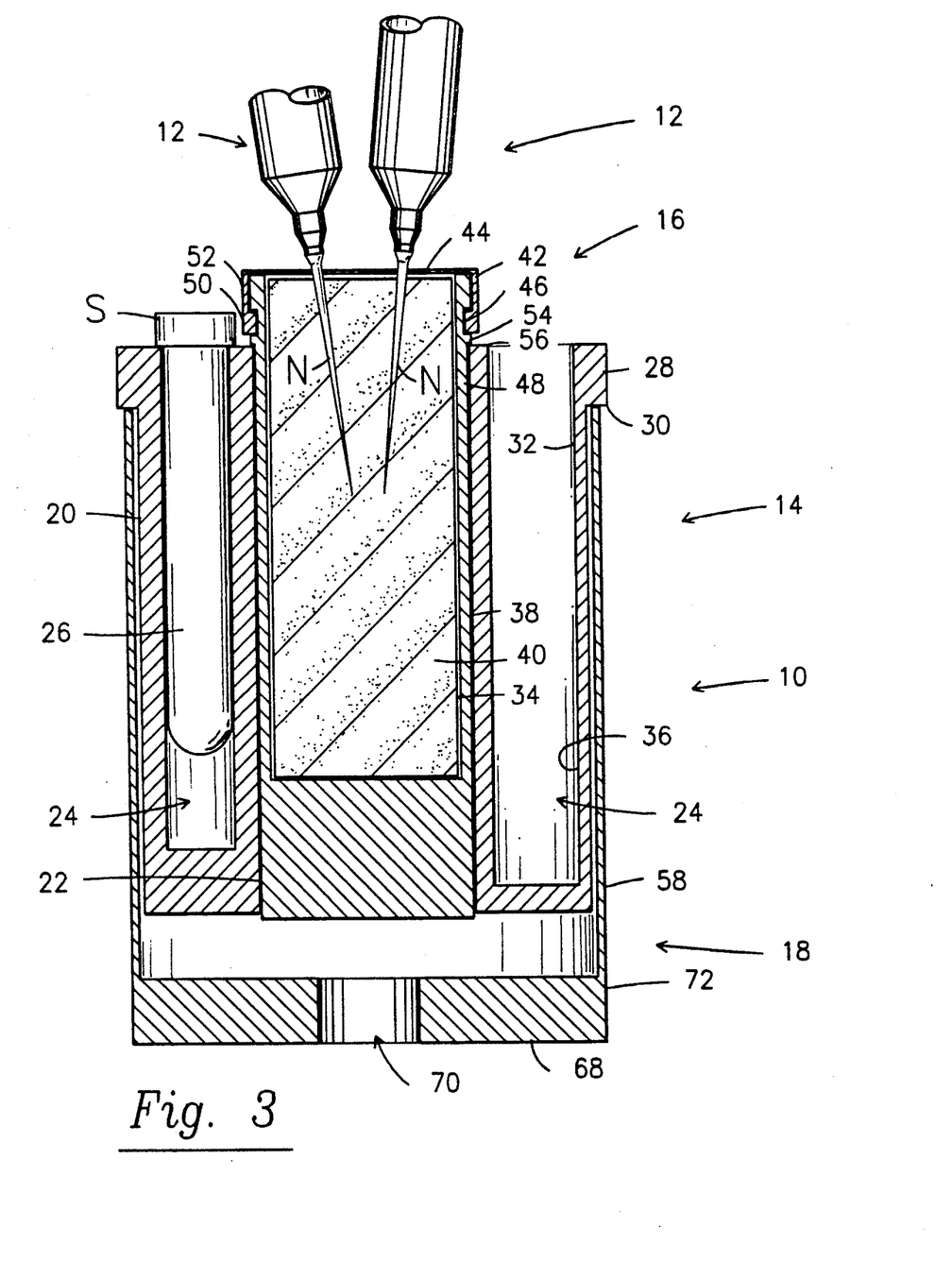
FIG. 3 is a cross-sectional view of the receptacle of the present invention taken along line 3—3 of FIG. 2.

As shown in FIGS. 1 through 3, the present invention relates to a receptacle generally indicated as 10 to support and retain a plurality of hypodermic needle and syringe combinations each generally indicated as 12 (FIG. 3) to prevent the accidental or inadvertant pricking of the care taker or patient after use.

As shown in FIGS. 1 through 3, the receptacle 10 comprises an outer receptacle support generally indicated as 14, an inner disinfectant canister generally indicated as 16 and a mounting means generally indicated as 18.

As shown in FIGS. 1 through 3, the outer receptacle support 14 comprises a lower substantially cylindrical body 20 including a centrally disposed substantially cylindrical canister recess 22 extending substantially the entire length thereof and a plurality of peripherally disposed substantially cylindrical liquid retaining tube recesses each indicated as 24 configured to selectively receive and support the inner disinfectant canister 16 and a plurality of liquid retaining tubes each indicated as 26 respectively. An upper receptacle support 28 comprising a support surface or ledge 30 is formed about the upper periphery 32 of the lower substantially cylindrical body 20 to engage the mounting means 18 when the outer receptacle support 14 is mounted thereon. The outer receptacle support 14 is constructed of 60 durometer urethane. This provides sufficient strength and resilience to protect the inner disinfectant canister 16 and liquid retaining tubes 26; while, having adequate memory such that the interior wall of the centrally disposed substantially cylindrical canister recess 22 and the interior walls of the plurality of peripherally disposed substantially cylindrical liquid tube recesses 24 indicated as 34 and 36 respectively are resilient to engage and secure the inner disinfectant canister 16 and liquid retaining tubes 26 within the centrally disposed substantially cylindrical canister recess 22 and the plurality of peripherally disposed substantially cylindrical liquid tube recesses 24 respectively.

As shown in FIGS. 1 through 3, the inner disinfectant canister 16 comprising a substantially cylindrical tube 38 to operatively house a porous element 40 of wet foam permeated with a disinfectant solution and a closure cap 42 including a penetrable membrane 44 to receive the used hypodermic needles each indicated as N therethrough to support and retain the used hypodermic needles N in the disinfectant solution. An annular groove 46 is formed about the upper periphery 48 of the substantially cylindrical tube 38 to operatively receive an annular lip 50 extending inwardly form an annular skirt 52 extending downwardly from the penetrable membrane 44 to secure the closure cap 42 to the substantially cylindrical tube 38. A support ledge or stop 54 extends outwardly from the upper periphery 48 of the substantially cylindrical tube 38 to engage the upper edge 56 of the centrally disposed substantially cylindrical recess 22. The penetrable membrane 44 is substantially one-sixteenth (1/16") inches in thickness of urethane of between 25 and 30 durometers. This particular thickness and hardness permits relative easy penetration of the penetrable membrane 44 by the needles N without tearing and strong enough to support the used hypodermic needle and syringe combinations 12 in a substantially vertical orientation or disposition.

As shown in FIGS. 1 through 3, the mounting means 18 comprises a substantially cylindrical mounting sleeve 58 to receive the lower substantially cylindrical body 20 therein, a mounting plate 60 fixed to the rear portion of the substantially cylindrical mount sleeve 58 by rivets 62 or the like and a mounting bracket 64 including a slot 66 to selectively receive the mounting plate 60 therein. A floor or bottom 68 having a centrally disposed aperture 70 formed therethrough may be formed across the lower periphery 72 of the substantially cylindrical mounting sleeve 58.

With the mounting means 18 attached to a wall W or other supporting surface, the outer receptacle support 14 and inner disinfectant canister 16 are operatively mounted thereon.

In use, the care taker withdraws blood or other body fluids that are injected through stoppers S into one or more of the plurality of liquid retaining tubes 26 operatively supported in the outer receptacle support 14. After the care taker has completed using the hypodermic needle and syringe combination 12, the hypodermic needle N is forced through the penetrable membrane 44 into the substantially cylindrical tube 38 and submerged in the disinfectant solution and retained in the porous element 40 to prevent accidental or inadvertent contact with the care taker or patient. Excess body or other body fluids may be injected into the substantially cylindrical tube 38. Moreover, the porous element 40 plugs the distal ends of the needles N.

The outer receptacle support 14 and inner disinfectant canister 16 are removed from the mounting bracket 64 after use. The plurality of liquid retaining tubes 26 may be removed from the outer receptacle support 14 for testing of the liquids stored therein; while, the inner disinfectant canister 16 may be removed from the outer receptacle support 14 for disposal of the used hypodermic needle and syringe combinations 12.

Figure 4:
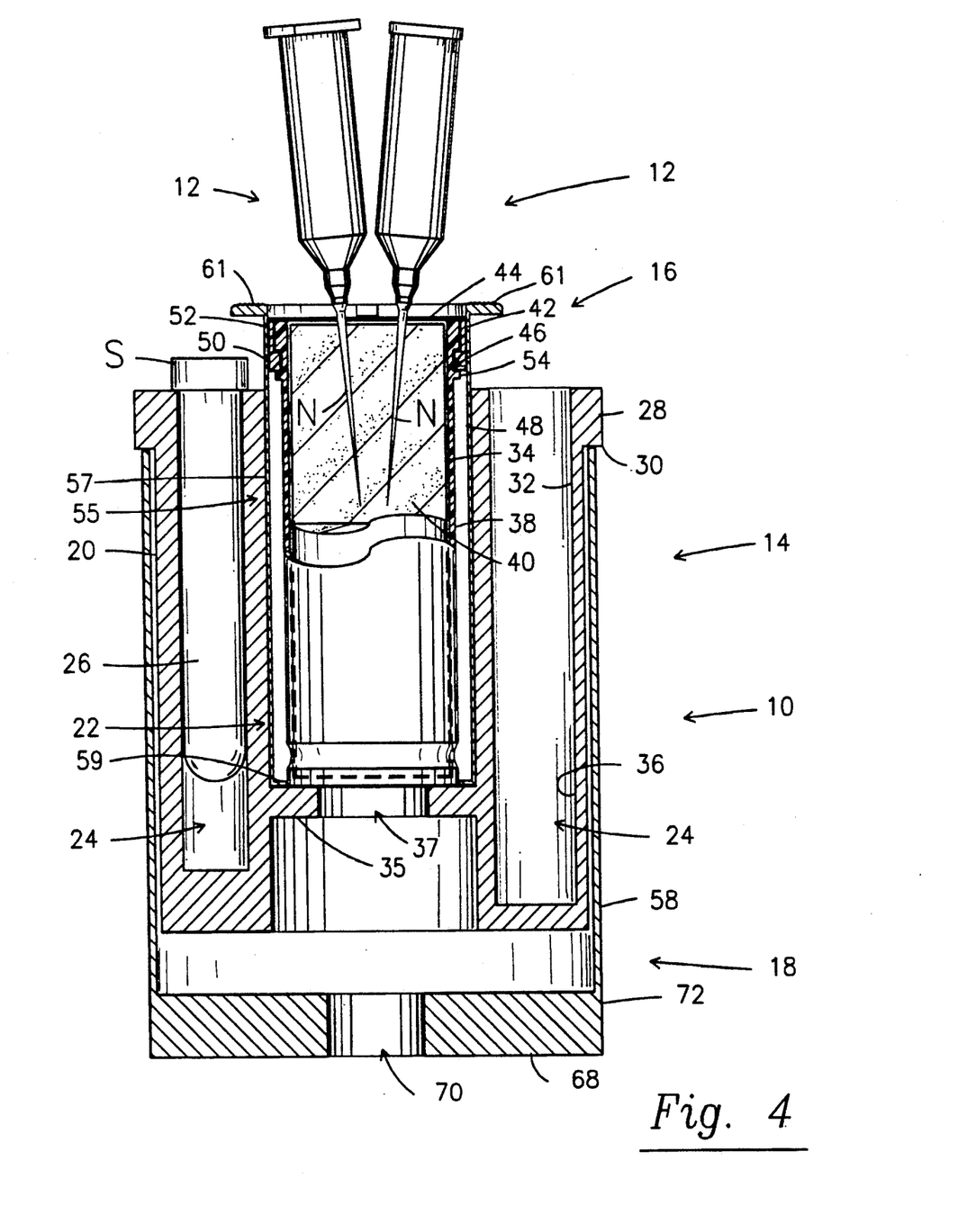
FIG. 4 is a cross-sectional view of an alternate embodiment of the receptacle of the present invention with the protective sheath or sleeve in the first or lower position.
Figure 5:
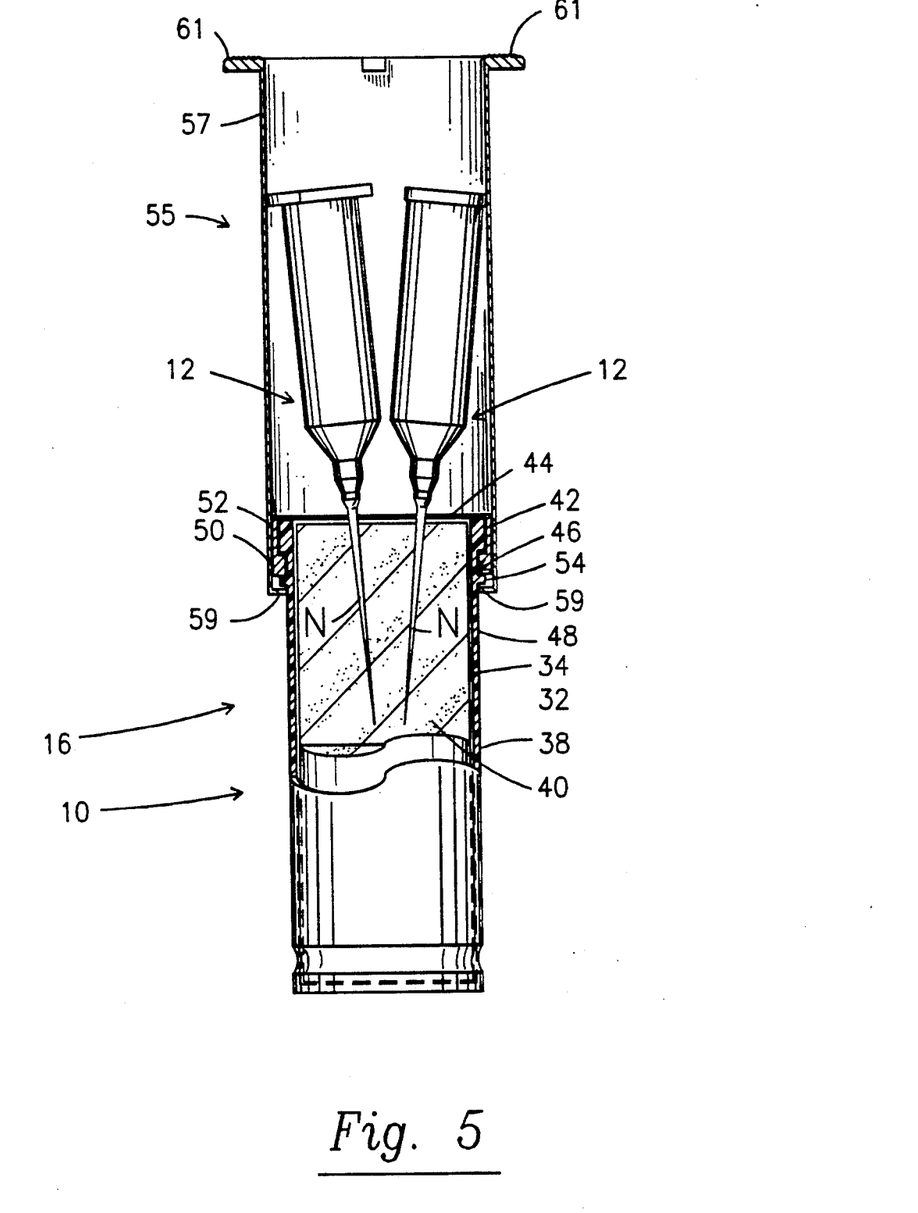
FIG. 5 is a partial cross-sectional view of the alternate embodiment of the receptacle of the present invention shown in FIG. 4 with the protective sheath or sleeve in the second or upper position.

FIGS. 4 and 5 show an alternate embodiment of receptacle 10 comprising the outer receptacle support generally indicated as 14 and the inner disinfectant canister generally indicated as 16 and the mounting means generally indicated as 18 similarly constructed to the receptacle 10 shown in FIGS. 1 through 3 except as indicated below.

As shown in FIGS. 4 and 5, the outer receptacle support 14 comprises a lower substantially cylindrical body 20 including a centrally disposed substantially cylindrical canister recess 22 extending therethrough and a plurality of peripherally disposed substantially cylindrical liquid retaining tube recesses each indicated as 24 configured to selectively receive and support the inner disinfectant canister 16 and a plurality of liquid retaining tubes each indicated as 26 respectively. An upper receptacle support 28 comprising a support surface or ledge 30 is formed about the upper periphery 32 of the lower substantially cylindrical body 20 to engage the mounting means 18 when the outer receptacle support 14 is mounted thereon. The outer receptacle support 14 is constructed of 60 durometer urethane. This provides sufficient strength and resilience to protect the inner disinfectant canister 16 and liquid retaining tubes 26; while, having adequate memory such that the interior wall of the centrally disposed substantially cylindrical canister recess 22 and the interior walls of the plurality of peripherally disposed substantially cylindrical liquid tube recesses 24 indicated as 34 and 36 respectively are resilient to engage and secure the inner disinfectant canister 16 and liquid retaining tubes 26 within the centrally disposed substantially cylindrical canister recess 22 and the plurality of peripherally disposed substantially cylindrical liquid tube recesses 24 respectively. A canister support shelf 35 having an aperture 37 formed therethrough is formed in the lower portion of the substantially cylindrical canister recess 22 to support the inner disinfectant canister 16 thereon.

As shown in FIGS. 4 and 5, the inner disinfectant canister 16 comprising a substantially cylindrical tube 38 to operatively house a porous element 40 of wet foam permeated with a disinfectant solution and a closure cap 42 including a penetrable membrane 44 to receive the used hypodermic needles each indicated as N therethrough to support and retain the used hypodermic needles N in the disinfectant solution. An annular groove 46 is formed about the upper periphery 48 of the substantially cylindrical tube 38 to operatively receive an annular lip 50 extending inwardly from an annular skirt 52 extending downwardly from the penetrable membrane 44 to secure the closure cap 42 to the substantially cylindrical tube 38. A ledge or stop element 54 extends outwardly from the upper periphery 48 of the substantially cylindrical tube 38 to engage a portion of a protective sheath or sleeve generally indicated as 55 as described more fully hereinafter. The penetrable membrane 44 is substantially one-sixteenth (1/16") inches in thickness of urethane of between 25 and 30 durometers. This particular thickness and hardness permits relative easy penetration of the penetrable membrane 44 by the needles N without tearing and strong enough to support the used hypodermic needle and syringe combinations 12 in a substantially vertical orientation or disposition.

The protective sheath or sleeve 55 comprises a substantially cylindrical hollow member 57 having a stop member 59 extending inwardly from the lower portion thereof and at least one tab 61 extending outwardly from the upper portion thereof to facilitate movement of the protective sheath or sleeve 55 between a first or lower position (FIG. 4) and a second or upper position (FIG. 5) to selectively engage the ledge or stop element 54 as described more fully hereinafter. The protective sheath or sleeve 55 is slidably mounted in surrounding relationship relative to the substantially cylindrical tube 38 such that when the first or lower position used hypodermic needle and syringe combinations 12 are securely placed in the receptacle 10 and when in the second or upper portion the used hypodermic needle and syringe combinations 12 are encased or enclosed therein.

Use is similar to that of the receptacle 10 shown in FIGS. 1 through 3 except that when the care taker has completed using a hypodermic needle and syringe combination 12 and with the substantially cylindrical protective sheath or sleeve 55 in the first or lower position, the hypodermic needle N is forced through the penetrable membrane 44 into the substantially cylindrical tube 38 and submerged in the disinfectant solution to prevent accidental or inadvertent contact with the care taker or patient. After the medical procedure is completed, the inner disinfectant canister 16 may be removed from the outer receptacle support 14 for disposal of the used hypodermic needle and syringe combinations 12 with the substantially cylindrical protective sheath or sleeve 55 in the second or upper position. The ledge or stop element 54 and stop member 59 cooperatively form an upper sleeve stop means to limit or restrict the upward movement of the substantially cylindrical protective sheath or sleeve 55 relative to the substantially cylindrical tube 38.

Figure 6:
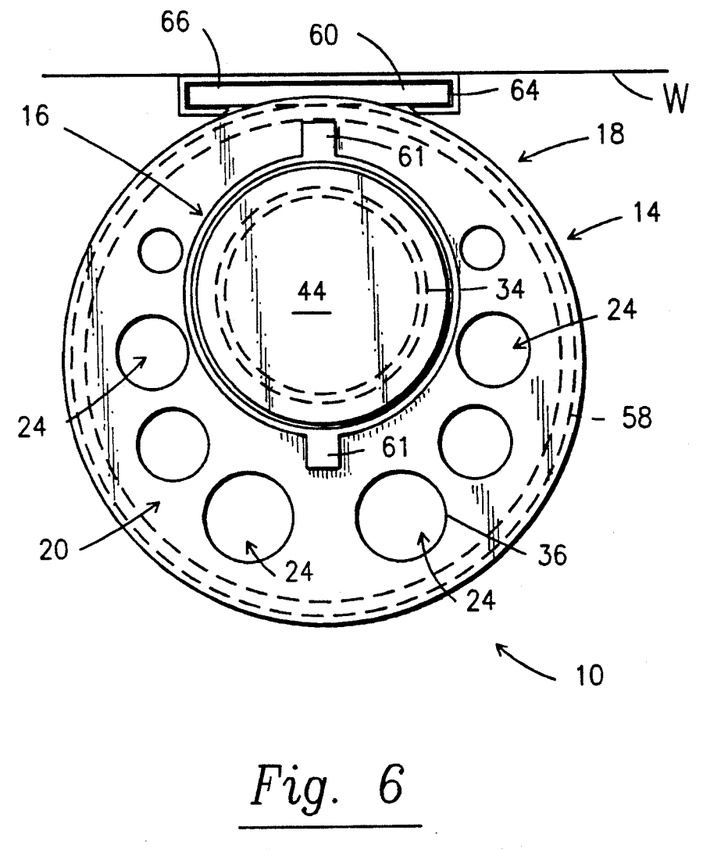
FIG. 6 is an exploded view of another alternate embodiment of the receptacle of the present invention.

The alternate embodiment of the receptacle 10 shown in FIG. 6 is substantially identical to the structure shown in FIGS. 1 through 3 or FIGS. 4 and 5 except that the cylindrical canister recess 22' is offset relative to the central longitudinal axis of the lower substantially cylindrical body 20.

Figure 7:
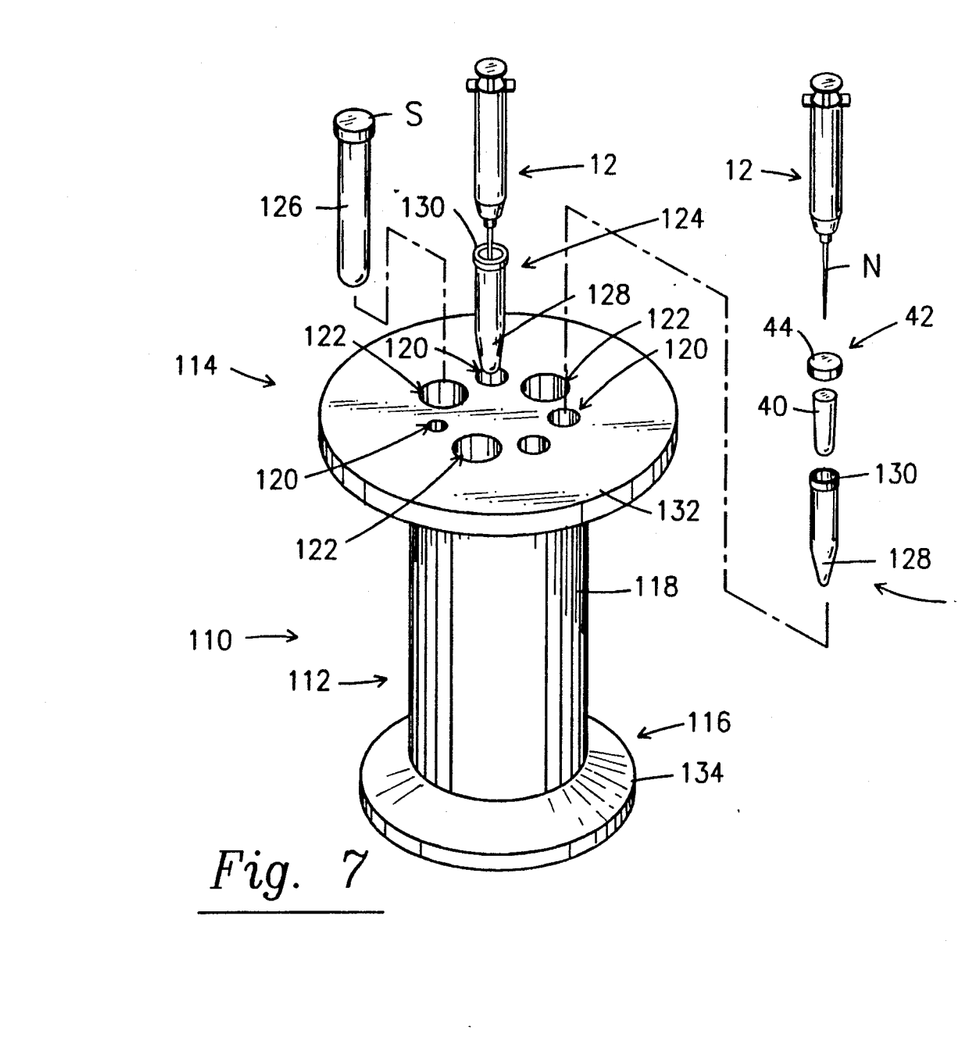
FIG. 7 is an exploded perspective view of still another embodiment of the receptacle of the present invention.
Figure 8:
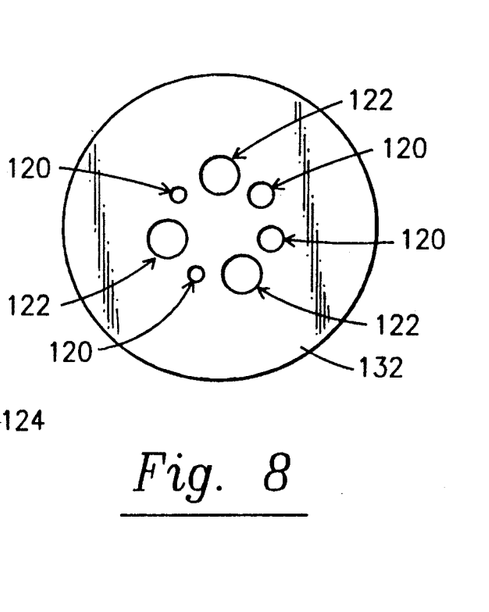
FIG. 8 is a top view of the alternate embodiment of the receptacle of the present invention shown in FIG. 7.

FIGS. 7 and 8 show still another alternate embodiment of the receptacle generally indicated as 110 comprising a receptacle support generally indicated as 112 having an upper protective hand guard generally indicated as 114 and a lower base generally indicated as 116 disposed at opposite ends thereof.

As shown in FIGS. 7 and 8, the receptacle support 112 comprises a substantially cylindrical body 118 including a plurality of substantially cylindrical canister recesses each indicated as 120 and a plurality of substantially cylindrical liquid retaining tube recesses each indicated as 122 configured to selectively receive and support a corresponding plurality of needle canisters each generally indicated as 124 and a plurality of liquid retaining tubes each indicated as 126 respectively.

Each needle canister 124 comprising a tapered tube 128 and an enlarged funnel shaped needle guide 130. The tapered tube 128 may operatively house a porous element 40 of wet foam permeated with a disinfectant solution similar to the previous disclosed embodiments. A closure cap 42 including a penetrable membrane 44 to receive the used hypodermic needles N therethrough to support and retain the used hypodermic needles N in the disinfectant solution.

The upper protective hand guard 114 comprises a skirt or apron member 132 extending outwardly from the upper portion of the substantially cylindrical body 118 to protect the care taker's hand and arm from needle pricks as the user grasps the substantially cylindrical body 118 during use.

The lower base 116 comprises a flat lower surface 134 to support the receptacle 110 on a surface when not in use.

In use, the care taker withdraws blood or other body fluids that are injected through stoppers S into one or more of the plurality of liquid retaining tubes 126 operatively supported in the receptacle support 112. When the care taker has completed using the hypodermic needle and syringe combination 12, the hypodermic needle N is forced through the penetrable membrane 136, into the needle canister 124 and submerged in the disinfectant solution and retained in the porous element 40 to prevent accidental or inadvertant contact with the care taker or patient. Excess body or other body fluids may be injected into the needle canister 124. Moreover, the porous element 40 plugs the distal ends of the needles N. The plurality of liquid retaining tubes 126 may be removed from the receptacle support 112 for testing of the liquids stored therein and the needle canisters 124 may be removed from the receptacle support 112 for disposal of the used hypodermic needle and syringe combinations 12.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A receptacle to support and retain a plurality of used hypodermic needle and syringe combinations and a plurality of hollow tubes, said receptacle comprising an outer receptacle support including a canister recess housing a hollow inner canister and a plurality of peripherally-disposed tube recesses to house a corresponding plurality of hollow tubes such that body fluids drawn from a patient by a hypodermic needle and syringe combinations are injected into one or more of the hollow tubes for storage and transport, and a protective sleeve slidably disposed within said canister recess in surrounding relationship relative to said hollow inner canister and movable between a first position and second position such that when in said first position used hypodermic needle and syringe combinations are mounted on said receptacle by placing the needles of the used hypodermic needle and syringe combinations into said hollow inner canister and when in said second position the syringes of the used hypodermic needle and syringe combinations are at least partially disposed within said protective sleeve.

2. The receptacle of claim 1, wherein said protective sleeve comprises a hollow member having a stop member formed thereon to selectively engage a stop element formed on said hollow inner canister to limit the upward movement of said hollow member relative to said hollow inner canister when said protective sleeve is moved from said first position to said second position.

3. The receptacle of claim 2 wherein said hollow member includes at least one tab thereof to facilitate movement of said protective sleeve between said first position and said second position.

4. The receptacle of claim 1 wherein said hollow inner canister has a porous element disposed therein to receive used needles therein.

5. The receptacle of claim 4 wherein said porous element comprises a member permeated with a disinfectant solution to receive used hypodermic needles therethrough to support and retain the used hypodermic needles in the disinfectant solution.

6. The receptacle of claim 1 wherein said hollow inner canister comprises an open tube having a cap including a penetrable membrane mounted on said open tube to retain disinfectant solution and excess body fluids therein wherein said penetrable membrane can receive used hypodermic needles therethrough.

7. The receptacle of claim 6 wherein said hollow inner canister includes an annular groove formed thereon to operatively receive an annular lip extending inwardly from an annular skirt extending downwardly from said penetrable membrane to secure said cap to said open tube.

8. The receptacle of claim 1 further including a mounting means comprising a mounting sleeve to support said outer receptacle support therein and a mounting plate attached to said mounting sleeve to secure said receptacle to a support surface.

9. The receptacle of claim 8 wherein said outer receptacle support includes an upper receptacle support formed thereon to engage said mounting sleeve to support said outer receptacle support thereon.

10. A receptacle to support and retain a plurality of used hypodermic needle and syringe combinations, said receptacle comprising an outer receptacle support including a canister recess housing a hollow inner canister and a protective sleeve slidably disposed within said canister recess in surrounding relationship relative to said hollow inner canister and movable between a first position and a second position such that when in said first position used hypodermic needle and syringe combinations are mounted on said receptacle by placing the needles of the used hypodermic needle and syringe combinations into said hollow inner canister and when in said second position the used hypodermic needle and syringe combinations are at least partially disposed within said protective sleeve.

11. The receptacle of claim 10 wherein said protective sleeve comprises a hollow member having a stop member formed thereon to selectively engage a stop element formed on said hollow inner canister to limit movement of said hollow member relative to said hollow inner canister when said protective sleeve is moved from said first position to said second position.

12. The receptacle of claim 11 wherein said hollow member includes at least one tab formed thereon to facilitate movement of said protective sleeve between said first position and said second position.

13. The receptacle of claim 10 wherein said hollow inner canister has a porous element disposed therein to receive used needles therein.

14. The receptacle of claim 13 wherein said porous element comprises a member permeated with a disinfectant solution to receive used hypodermic needles therethrough to support and retain the used hypodermic needles in the disinfectant solution.

15. The receptacle of claim 10 wherein said hollow inner canister comprises an open tube having a cap including a penetrable membrane mounted on said open tube to retain disinfectant solution and excess body fluids therein wherein said penetrable membrane can receive used hypodermic needles therethrough.

16. The receptacle of claim 15 wherein said cap includes an annular skirt extending downwardly from said penetrable membrane and said hollow inner canister includes an annular groove formed thereon to operatively receive an annular lip extending inwardly from said annular skirt to secure said cap to said open tube.

17. The receptacle of claim 10 further including a mounting means comprising a mounting sleeve to support said outer receptacle support therein and a mounting plate attached to said mounting sleeve to secure said receptacle to a support surface.

18. The receptacle of claim 17 wherein said outer receptacle support includes an upper receptacle support formed to engage said mounting sleeve to support said outer receptacle support.

19. A receptacle to support and retain a plurality of used hypodermic needle and syringe combinations and a plurality of hollow tubes, said receptacle comprising an outer receptacle support including a canister recess housing a hollow inner canister and a plurality of peripherally-disposed tube recesses to house a corresponding plurality of hollow tubes such that body fluids drawn from a patient by a hypodermic needle and syringe combination are injected into one or more of the hollow tubes for storage and transport, and a protective sleeve slidably disposed in surrounding relationship relative to said hollow inner canister and movable between a first position and a second position such that when in said first position used hypodermic needle and syringe combinations are mounted on said receptacle by placing the needles of the used hypodermic needle and syringe combinations into said hollow inner canister and when in said second position the syringes of the used hypodermic needle and syringe combinations are at least partially disposed within said protective sleeve, said protective sleeve comprises a hollow member having a stop member formed thereon to selectively engage a stop element formed on said hollow inner canister to limit movement of said hollow member relative to said hollow inner canister when said protective sleeve is moved from said first position to said second position.

20. The receptacle of claim 19 wherein said hollow member includes at least one tab formed thereon to facilitate movement of said protective sleeve between said first position and said second position.

21. The receptacle of claim 19 wherein said hollow inner canister has a porous element disposed therein to receive used needles therein.

22. The receptacle of claim 21 wherein said porous element comprises a member permeated with a disinfectant solution to receive used hypodermic needles therethrough to support and retain the used hypodermic needles in the disinfectant solution.

23. A receptacle to support and retail a plurality of used hypodermic needle and syringe combinations and a plurality of hollow tubes, said receptacle comprising an outer receptacle support including a canister recess housing a hollow inner canister and a plurality of peripherally-disposed tube recesses to house a corresponding plurality of hollow tubes such that body fluids drawn from a patient by a hypodermic needle and syringe combination are injected into one or more of the hollow tubes for storage and transport, and a protective sleeve slidably disposed in surrounding relationship relative to said hollow inner canister and movable between a first position and a second position such that when in said first position used hypodermic needle and syringe combinations are mounted on said receptacle by placing the needles of the used hypodermic needle and syringe combinations into said hollow inner canister and when in said second position the syringes of the used hypodermic needle and syringe combinations are at least partially disposed within said protective sleeve, said hollow inner canister comprises an open tube having a cap including a penetrable membrane mounted on said open tube to retain disinfectant solution and excess body fluids therein wherein said penetrable membrane can receive used hypodermic needles therethrough, said hollow inner canister includes an annular groove formed thereon to operatively receive an annular lip extending inwardly from an annular skirt extending downwardly from said penetrable membrane to secure said cap to said open tube.

24. A receptacle to support and retail a plurality of used hypodermic needle and syringe combinations and a plurality of hollow tubes, said receptacle comprising an outer receptacle support including a canister recess housing a hollow inner canister and a plurality of peripherally-disposed tube recesses to house a corresponding plurality of hollow tubes such that body fluids drawn from a patient by a hypodermic needle and syringe combinations are injected into one or more of the hollow tubes for storage and transport, and a protective sleeve slidably disposed in surrounding relationship relative to said hollow inner canister and movable between a first position and a second position such that when in said first position used hypodermic needle and syringe combinations are mounted on said receptacle by placing the needles of the used hypodermic needle and syringe combinations into said hollow inner canister and when in said second position the syringes of the used hypodermic needle and syringe combinations are at least partially disposed within said protective sleeve, said mounting means comprising a mounting sleeve to support said outer receptacle support therein and a mounting plate attached to said mounting sleeve to secure said receptacle to a support surface.

25. The receptacle of claim 24 wherein said outer receptacle support includes an upper receptacle support formed thereon to engage said mounting sleeve to support said outer receptacle support thereon.

26. A receptacle to support and retain a plurality of used hypodermic needle and syringe combinations, said receptacle comprising an outer receptacle support including a canister recess housing a hollow inner canister and a protective sleeve slidably disposed in surrounding relationship relative to said hollow inner canister and movable between a first position and a second position such that when in said first position used hypodermic needle and syringe combinations are mounted on said receptacle by placing the needles of the used hypodermic needle and syringe combinations into said hollow inner canister and when in said second position the used hypodermic needle and syringe combinations are at least partially disposed within said protective sleeve, said protective sleeve comprises a hollow member having a stop member formed thereon to selectively engage a stop element formed on said hollow inner canister to limit the said hollow member relative to said hollow inner canister when said protective sleeve is moved from said first position to said second position.

27. The receptacle of claim 26 wherein said hollow member includes at least one tab to facilitate movement of said protective sleeve between said first position and said second position.

28. The receptacle of claim 26 wherein said hollow inner canister has a porous element disposed therein to receive used needles therein.

29. The receptacle of claim 28 wherein said porous element comprises a member permeated with a disinfectant solution to receive used hypodermic needles therethrough to support and retain the used hypodermic needles therethrough to support and retain the used hypodermic needles in the disinfectant solution.

30. A receptacle to support and retain plurality of used hypodermic needle and syringe combinations and a plurality of hollow tubes, said receptacle comprising an outer receptacle support including a canister recess housing a hollow inner canister and a plurality of peripherally-disposed tube recesses to house a corresponding plurality of hollow tubes such that body fluids drawn from a patient by a hypodermic needle and syringe combination are injected into one or more of the hollow tubes for storage and transport and a protective sleeve slidably disposed in surrounding relationship relative to said hollow inner canister and movable between a first position and a second position such that when in said first position used hypodermic needle and syringe combinations are mounted on said receptacle by placing the needles of the used hypodermic needle and syringe combinations into said hollow inner canister and when in said second position the syringes of the used hypodermic needle and syringe combinations are at least partially disposed within said protective sleeve, said hollow inner canister comprises an open tube having a cap including a penetrable membrane mounted on said open tube to retain disinfectant solution and excess body fluids therein wherein said penetrable membrane can receive used hypodermic needles therethrough and said cap includes an annular skirt extending downwardly from said penetrable membrane and said hollow inner canister includes an annular groove formed thereon to operatively receive an annular lip extending inwardly from said annular skirt to secure said cap to said open tube.

31. A receptacle to support and retain a plurality of used hypodermic needle and syringe combinations said receptacle comprising an outer receptacle support including a canister recess housing a hollow inner canister, a protective sleeve slidably disposed in surrounding relationship relative to said hollow inner canister and movable between a first position and a second position such than when in said first position used hypodermic needle and syringe combinations are mounted on said receptacle by placing the needles of the used hypodermic needle and syringe combinations into said hollow inner canister and when in said second position the used hypodermic needle and syringe combinations are at least partially disposed within said protective sleeve and further including a mounting means comprising a mounting sleeve to support said outer receptacle support therein and a mounting plate attached to said mounting sleeve to secure said receptacle to a support surface.

32. The receptacle of claim 31 wherein said outer receptacle support includes an upper receptacle support formed thereon to engage said mounting sleeve to support said outer receptacle support.

* * * * *